United States Patent
Ghiasi et al.

(10) Patent No.: US 11,116,412 B2
(45) Date of Patent: Sep. 14, 2021

(54) ROBUST, CLINICAL-GRADE TRANSABDOMINAL FETAL PULSE OXIMETRY

(71) Applicant: The Regents of the University of California, Oakland, CA (US)

(72) Inventors: Soheil Ghiasi, Davis, CA (US); Daniel Fong, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 171 days.

(21) Appl. No.: 16/347,532

(22) PCT Filed: Nov. 11, 2017

(86) PCT No.: PCT/US2017/062782
§ 371 (c)(1),
(2) Date: May 3, 2019

(87) PCT Pub. No.: WO2018/094391
PCT Pub. Date: May 24, 2018

(65) Prior Publication Data
US 2020/0245879 A1    Aug. 6, 2020

Related U.S. Application Data

(60) Provisional application No. 62/424,789, filed on Nov. 21, 2016.

(51) Int. Cl.
*A61B 5/024* (2006.01)
*A61B 5/00* (2006.01)

(52) U.S. Cl.
CPC ...... *A61B 5/02411* (2013.01); *A61B 5/02416* (2013.01); *A61B 5/02438* (2013.01);
(Continued)

(58) Field of Classification Search
CPC ............ A61B 5/02411; A61B 5/02416; A61B 5/02438; A61B 5/02444; A61B 5/725;
(Continued)

(56) References Cited

U.S. PATENT DOCUMENTS

| | | | |
|---|---|---|---|
| 7,047,055 B2 * | 5/2006 | Boas | A61B 5/14542 600/338 |
| 8,644,900 B2 | 2/2014 | Balberg et al. | |

(Continued)

FOREIGN PATENT DOCUMENTS

WO    2020010276 A1    1/2020

OTHER PUBLICATIONS

International Search Report and Written Opinion PCT/US2017/062782, dated Feb. 19, 2018, Korean International Application Division Commisioner.

*Primary Examiner* — Lindsey G Wehrheim
(74) *Attorney, Agent, or Firm* — Park, Vaughan, Fleming & Dowler LLP

(57) ABSTRACT

The system determines a fetal blood oxygenation level by activating two or more light sources, having different wavelengths, which are positioned on the maternal abdomen of a pregnant mammal to direct light into a maternal abdomen toward a fetus. The system then receives a maternal signal from a first photodetector, which is positioned on the maternal abdomen to receive reflected light that traverses maternal tissue. The system also receives a mixed signal from a second photodetector, which is positioned on the maternal abdomen to receive reflected light that traverses both maternal and fetal tissue. The system performs a filtering operation that removes maternal signal components from the mixed signal to produce a fetal signal. The system determines the fetal blood oxygenation level by performing a pulse-oximetry computation on the fetal signal. The system (Continued)

dynamically adjusts operational parameters in the face of changing variables, such as fetus position and depth.

32 Claims, 14 Drawing Sheets

(52) U.S. Cl.
CPC .......... *A61B 5/02444* (2013.01); *A61B 5/725* (2013.01); *A61B 5/7257* (2013.01); *A61B 2503/02* (2013.01)

(58) Field of Classification Search
CPC .............. A61B 5/7257; A61B 2503/02; A61B 5/14542; A61B 5/4362; A61B 5/1464
See application file for complete search history.

(56) References Cited

U.S. PATENT DOCUMENTS

| | | | |
|---|---|---|---|
| 2004/0116789 A1* | 6/2004 | Boas | A61B 5/14542 600/338 |
| 2006/0189862 A1 | 8/2006 | Casciani et al. | |
| 2009/0281402 A1 | 11/2009 | Chance | |
| 2010/0137727 A1 | 6/2010 | Sameni et al. | |
| 2011/0218413 A1* | 9/2011 | Wang | A61B 5/1464 600/324 |
| 2018/0256088 A1 | 9/2018 | Ray | |

* cited by examiner

| *Maternal Dermal* | $\lambda_{700nm}$ | $\lambda_{735nm}$ | $\lambda_{800nm}$ | $\lambda_{850nm}$ | $\lambda_{900nm}$ |
|---|---|---|---|---|---|
| $\mu_a$ (cm$^{-1}$) | 0.190 | 0.170 | 0.126 | 0.125 | 0.127 |
| $\mu_s'$ (cm$^{-1}$) | 23.2 | 23.0 | 19.4 | 17.7 | 17.5 |
| z (cm) | 0.15 | | | | |
| *Maternal Subdermal* | $\lambda_{700nm}$ | $\lambda_{735nm}$ | $\lambda_{800nm}$ | $\lambda_{850nm}$ | $\lambda_{900nm}$ |
| $\mu_a$ (cm$^{-1}$) | 0.080 | 0.085 | 0.080 | 0.088 | 0.122 |
| $\mu_s'$ (cm$^{-1}$) | 12.2 | 12.0 | 11.6 | 11.1 | 10.9 |
| z (cm) | 0.9 - 3.9 | | | | |
| *Maternal Uterus* | $\lambda_{700nm}$ | $\lambda_{735nm}$ | $\lambda_{800nm}$ | $\lambda_{850nm}$ | $\lambda_{900nm}$ |
| $\mu_a$ (cm$^{-1}$) | 0.180 | 0.160 | 0.105 | 0.100 | 0.120 |
| $\mu_s'$ (cm$^{-1}$) | 11.5 | 10.8 | 9.10 | 8.15 | 7.40 |
| z (cm) | 0.85 | | | | |
| *Amniotic Fluid* | $\lambda_{700nm}$ | $\lambda_{735nm}$ | $\lambda_{800nm}$ | $\lambda_{850nm}$ | $\lambda_{900nm}$ |
| $\mu_a$ (cm$^{-1}$) | 0.007 | 0.025 | 0.033 | 0.042 | 0.064 |
| $\mu_s'$ (cm$^{-1}$) | 0.1 | 0.1 | 0.1 | 0.1 | 0.1 |
| z (cm) | 0.1 | | | | |
| *Fetal Scalp* | $\lambda_{700nm}$ | $\lambda_{735nm}$ | $\lambda_{800nm}$ | $\lambda_{850nm}$ | $\lambda_{900nm}$ |
| $\mu_a$ (cm$^{-1}$) | 0.157 | 0.157 | 0.158 | 0.157 | 0.156 |
| $\mu_s'$ (cm$^{-1}$) | 7.32 | 6.81 | 5.90 | 6.23 | 5.70 |
| z (cm) | 0.2 | | | | |
| *Fetal Arterial* | $\lambda_{700nm}$ | $\lambda_{735nm}$ | $\lambda_{800nm}$ | $\lambda_{850nm}$ | $\lambda_{900nm}$ |
| $\mu_a$ (cm$^{-1}$) | 0.174 | 0.175 | 0.144 | 0.155 | 0.178 |
| $\mu_s'$ (cm$^{-1}$) | 36.0 | 35.0 | 32.0 | 30.0 | 28.0 |
| z (cm) | 0.1 | | | | |
| *Fetal Skull* | $\lambda_{700nm}$ | $\lambda_{735nm}$ | $\lambda_{800nm}$ | $\lambda_{850nm}$ | $\lambda_{900nm}$ |
| $\mu_a$ (cm$^{-1}$) | 0.208 | 0.210 | 0.213 | 0.215 | 0.260 |
| $\mu_s'$ (cm$^{-1}$) | 11.9 | 10.9 | 10.0 | 9.1 | 8.4 |
| z (cm) | 0.15 | | | | |
| *Fetal Brain* | $\lambda_{700nm}$ | $\lambda_{735nm}$ | $\lambda_{800nm}$ | $\lambda_{850nm}$ | $\lambda_{900nm}$ |
| $\mu_a$ (cm$^{-1}$) | 0.215 | 0.187 | 0.160 | 0.132 | 0.150 |
| $\mu_s'$ (cm$^{-1}$) | 13.4 | 12.2 | 11.0 | 9.8 | 9.0 |
| z (cm) | 100.0 | | | | |

FIG. 3B

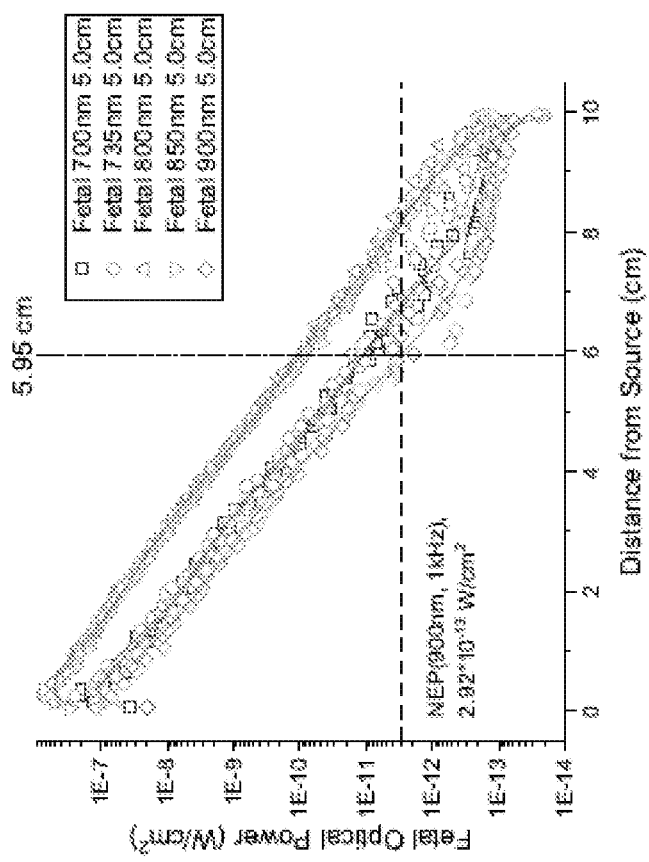
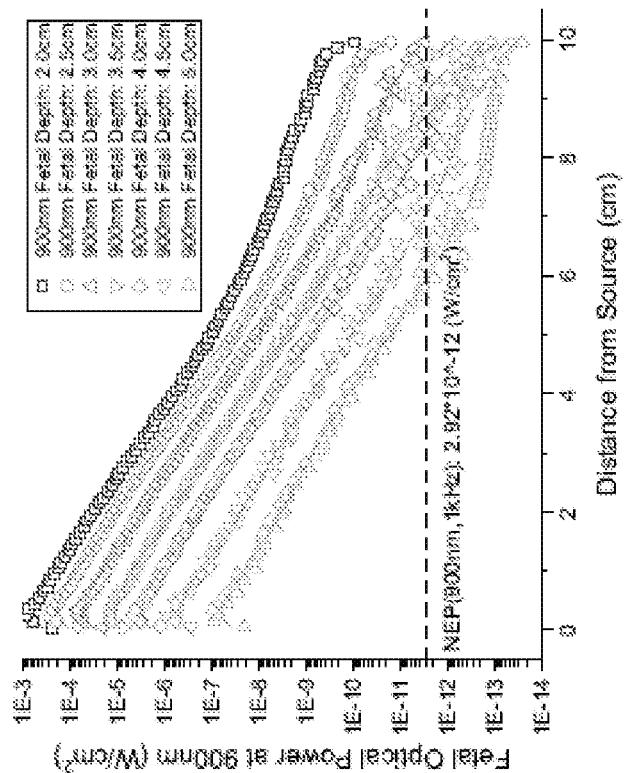
FIG. 4F
FIG. 4E

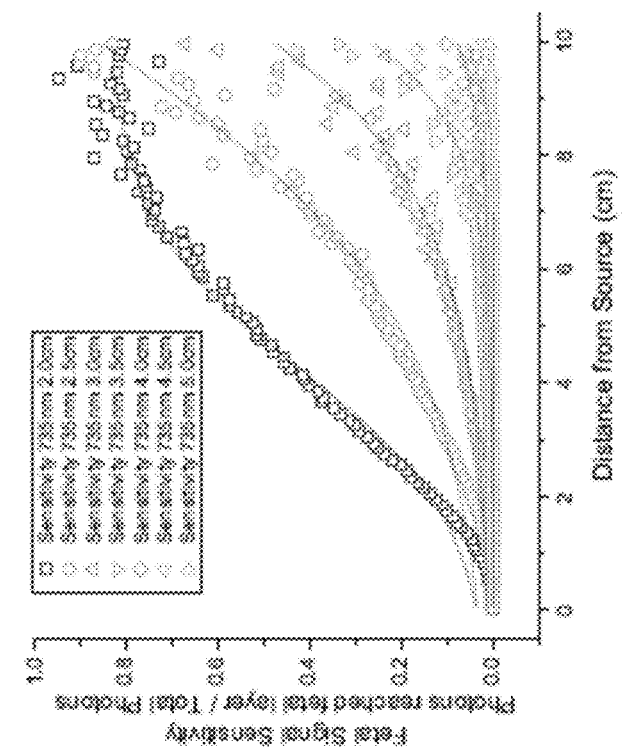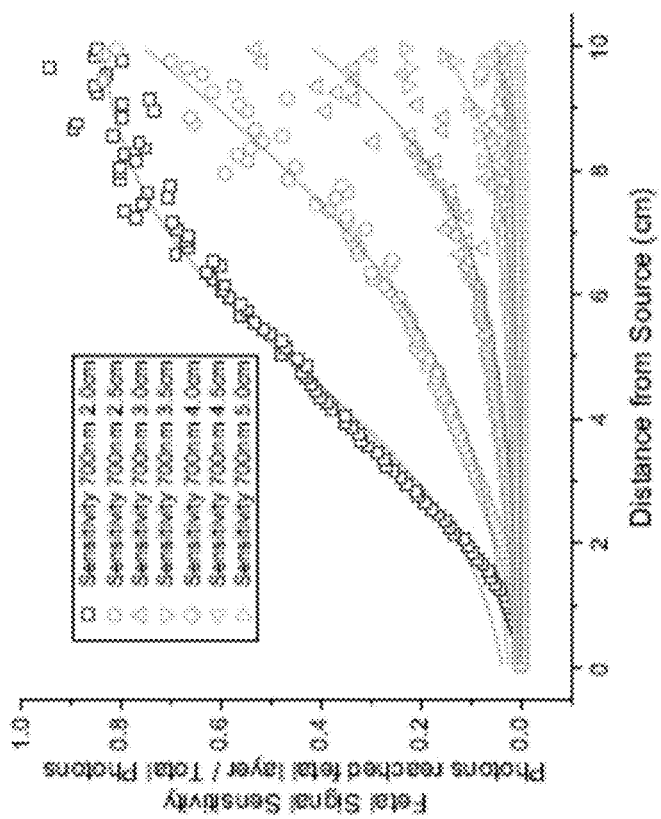
FIG. 5A
FIG. 5B

ROBUST, CLINICAL-GRADE TRANSABDOMINAL FETAL PULSE OXIMETRY

CROSS-REFERENCE TO RELATED APPLICATION

This application claims the benefit of U.S. Provisional Application Ser. No. 62/424,789, entitled "Method and Apparatus for Robust-Clinical-Grade Transabdominal Fetal Blood Oximetry," by inventor Soheil Ghiasi and Daniel Fong, Attorney Docket Number UC17-368-1PSP, filed on 21 Nov. 2016, the contents of which are incorporated by reference herein.

BACKGROUND

Field

The disclosed embodiments generally relate to non-invasive techniques for monitoring the health of a fetus in utero. More specifically, the disclosed embodiments relate to a technique for performing robust, clinical-grade transabdominal fetal pulse oximetry.

Related Art

The Caesarean section (C-section) rate in the US is nearly 40%, with many private practices reporting a rate of over 50%. The World Health Organization (WHO) has stated that "there is no justification for any region to have a Caesarean section rate higher than 10-15%." In 2015, a group of researchers studied the C-section rates of all 194 WHO member states as well as maternal and neonatal mortality, and concluded that a C-section rate of 19% results in optimal outcomes across the spectrum. (See G. Molina, T. G. Weiser, S. R. Lipsitz, et al. *Relationship between cesarean delivery rate and maternal and neonatal mortality*. JAMA, 314(21): 2263-2270, 12, 2015.) Partly in response, the Department of Health and Human Services has set a goal to reduce C-section rates in the US to 24% by 2020.

A C-section is a major abdominal surgery, which can add $25-50,000 to the cost of hospitalization for labor and delivery. In addition, one out of every 100 C-sections performed results in a major complication to the mother, such as a blood clot, post-operative wound infection, massive hemorrhage requiring a blood transfusion, and damage to adjacent organs such as the bladder or intestines. A woman is three to five times more likely to die from C-section-related complications versus a vaginal delivery. Moreover, children born via C-section have increased risks for some complications. There is an increased risk of death to the baby in the first year of life when born via C-section. Long term, these children also have an increased incidence of chronic lung conditions such as asthma, bronchopulmonary dysplasia, and interstitial lung disease. One study found that children born via C-section had a 22% higher incidence of asthma compared to children born via vaginal delivery. As such, it is desirable to avoid unnecessary C-sections, and work to reduce the national C-section rate to align with globally accepted norms.

Despite all of the medical advances during the past century, fetal monitoring during labor and delivery has not changed significantly over the past 50 years. Specifically, obstetricians continue to utilize a "one-size-fits-all" approach for monitoring fetal well-being using fetal heart rate monitoring. The current paradigm for fetal monitoring measures the fetal heart rate in relationship to uterine contractions. Sometimes a decrease in the fetal heart rate (fetal bradycardia) after a uterine contraction is suggestive of fetal distress, but it is often a normal physiological response. Because fetal bradycardia and fetal distress can sometimes lead to inadequate blood flow to the brain and subsequent anoxic brain injury, quickly removing the baby via C-section delivery (also known as an "emergency C-section") becomes a compelling option. There is clear evidence that this practice has led to unnecessarily inflated rates of C-section, and subsequent complications to the mother without decreasing the incidence of cerebral palsy or perinatal mortality of the fetus.

One factor that leads to excessive C-section rates is that fetal blood oxygenation data is not conveniently available during labor and delivery. Thus, obstetricians have to rely on the fetal heart rate as an imperfect measure to conservatively estimate fetal blood oxygenation.

Hence, what is needed is a practical technique for measuring fetal blood oxygenation without the drawbacks of existing techniques.

SUMMARY

The disclosed embodiments relate to a system that determines a fetal blood oxygenation level. During operation, the system activates two or more light sources, having different wavelengths, which are positioned on the maternal abdomen of a pregnant mammal to direct light into a maternal abdomen toward a fetus. The system then receives a maternal signal from a first photodetector, which is positioned on the maternal abdomen to receive reflected light that traverses maternal tissue. The system also receives a mixed signal from a second photodetector, which is positioned on the maternal abdomen to receive reflected light that traverses both maternal and fetal tissue. Next, the system performs a filtering operation that removes maternal signal components from the mixed signal to produce a fetal signal. Finally, the system determines the fetal blood oxygenation level by performing a pulse-oximetry computation on the fetal signal.

In some embodiments, the filtering operation discriminates between the maternal and fetal signals based on periodic variations in the maternal and fetal signals caused by arterial pulsations that are correlated with maternal and fetal heartbeats.

In some embodiments, while performing the filtering operation, the system first performs fast-Fourier transform (FFT) operations on the mixed and maternal signals to compute corresponding frequency-domain representations of the mixed and maternal signals. Next, the system infers a spectral density of the maternal pulse from the frequency-domain representation of the maternal signal; and then uses the inferred information to filter out the maternal signal from the mixed signal to produce the fetal signal.

In some embodiments, the system improves the fetal signal by adaptively adjusting filter parameters used to filter out the maternal signal.

In some embodiments, the two or more light sources emit light at two or more different wavelengths, including wavelengths, $\lambda_1$ and $\lambda_2$, which lie on opposite sides of the isosbestic point of an absorption curve for Hb and $HbO^2$. In these embodiments, the pulse oximetry computation is performed on an AC component of the fetal signal associated with pulsating fetal tissue, which includes blood, for each of the wavelengths $\lambda_1$ and $\lambda_2$, and a DC component of the fetal signal associated with non-pulsating fetal tissue for each of the wavelengths $\lambda_1$ and $\lambda_2$.

In some embodiments, the wavelength $\lambda_1$ substantially equals 735 nm, and the wavelength $\lambda_2$ substantially equals 850 nm.

In some embodiments, the system dynamically adjusts the maternal signal by calculating a statistical distribution of the maternal signal, which can include, but is not limited to: average, minimum, maximum and variance values for the maternal signal; and adjusting a gain of an amplifier for the maternal signal based on the calculated statistical distribution of the maternal signal.

In some embodiments, the system dynamically adjusts the mixed signal by periodically calculating a statistical distribution of the mixed signal, which can include, but is not limited to: average, minimum, maximum and variance values for the mixed signal; and adjusting a gain of an amplifier for the mixed signal based on the calculated statistical distribution of the mixed signal.

In some embodiments, after the fetal signal is produced, the system adjusts a source-detector distance by: determining a quality of the fetal signal through analysis of the strength of the fetal signal compared to noise in either the time-domain or the frequency-domain; and tuning an effective depth of penetration for the method by selecting a light-source-and-photodetector pair from a plurality of light sources and plurality of photodetectors located at different sites on the maternal abdomen, wherein the selection is based on the determined qualities of fetal signals associated with different light-source-and-photodetector pairs.

In some embodiments, the system additionally comprises one or more other measurement devices, which are configured to measure one or more of, a fetal heart rate, a maternal heart rate, and a maternal blood oxygenation level. In these embodiments, the system uses one or more of the measured fetal heart rate, the measured maternal heart rate and/or the measured maternal blood oxygenation level while determining the fetal blood oxygenation level.

In some embodiments, the two or more light sources include two or more near-infrared light-emitting diodes (LEDs) that emit light at two or more wavelengths.

In some embodiments, the first and second photodetectors comprise silicon photodiodes.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIG. 3B presents a table containing optical properties of the multi-layered tissue model in accordance with the disclosed embodiments.

FIGS. 4A-4F present graphs illustrating the fetal signal strength for various wavelengths in accordance with the disclosed embodiments.

FIGS. 5A-5F present graphs illustrating fetal signal sensitivity for various wavelengths in accordance with the disclosed embodiments.

DETAILED DESCRIPTION

The following description is presented to enable any person skilled in the art to make and use the present embodiments, and is provided in the context of a particular application and its requirements. Various modifications to the disclosed embodiments will be readily apparent to those skilled in the art, and the general principles defined herein may be applied to other embodiments and applications without departing from the spirit and scope of the present embodiments. Thus, the present embodiments are not limited to the embodiments shown, but are to be accorded the widest scope consistent with the principles and features disclosed herein.

The data structures and code described in this detailed description are typically stored on a computer-readable storage medium, which may be any device or medium that can store code and/or data for use by a computer system. The computer-readable storage medium includes, but is not limited to, volatile memory, non-volatile memory, magnetic and optical storage devices such as disk drives, magnetic tape, CDs (compact discs), DVDs (digital versatile discs or digital video discs), or other media capable of storing computer-readable media now known or later developed.

The methods and processes described in the detailed description section can be embodied as code and/or data, which can be stored in a computer-readable storage medium as described above. When a computer system reads and executes the code and/or data stored on the computer-readable storage medium, the computer system performs the methods and processes embodied as data structures and code and stored within the computer-readable storage medium. Furthermore, the methods and processes described below can be included in hardware modules. For example, the hardware modules can include, but are not limited to, application-specific integrated circuit (ASIC) chips, field-programmable gate arrays (FPGAs), Application-Specific Instruction Processors (ASIP), and other programmable-logic devices now known or later developed. When the hardware modules are activated, the hardware modules perform the methods and processes included within the hardware modules.

Details

Figure 1:
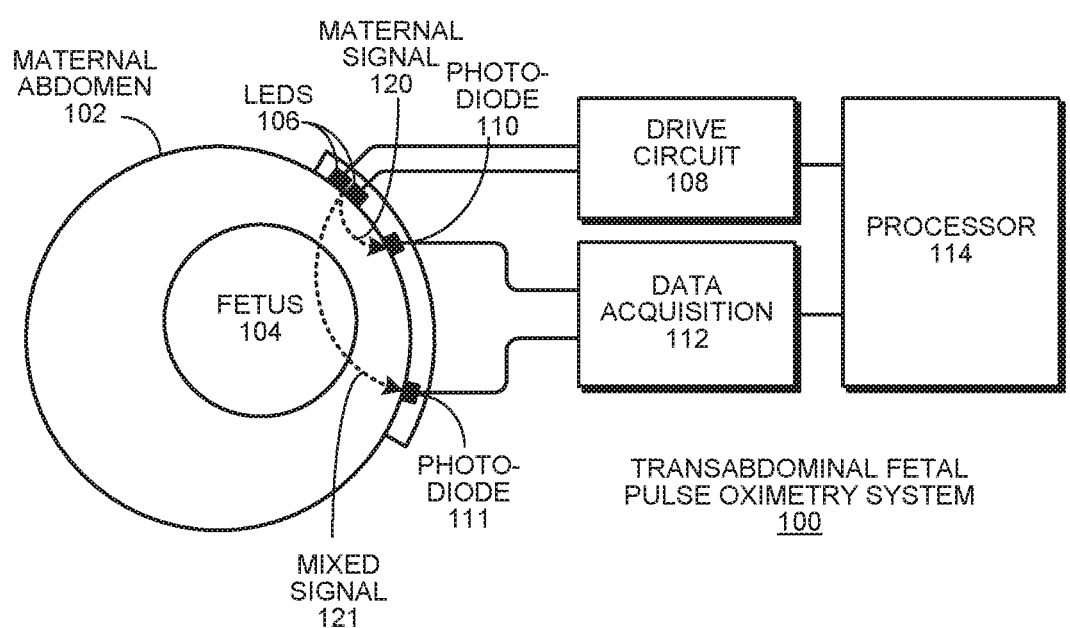
FIG. 1 illustrates a transabdominal fetal pulse oximetry system in accordance with the disclosed embodiments.

FIG. 1 illustrates a transabdominal fetal pulse oximetry system 100 in accordance with the disclosed embodiments. This system 100 includes a light source comprising a set of two or more light-emitting diodes (LEDs) 106, which emit light at two or more wavelengths. As illustrated in FIG. 1, LEDs 106 are positioned on a maternal abdomen 102 to direct light toward a fetus 104. Note that LEDs 106 are powered by a drive circuit, which operates under control of a processor 114. A first photodetector comprising a photodiode 110 is positioned on the maternal abdomen 102 to receive reflected light that traverses maternal tissue and in response produces a "maternal signal" 120. A second photodetector comprising a photodiode 111 is positioned on the maternal abdomen 102 to receive reflected light that traverses both maternal and fetal tissue and in response produces a "mixed signal" 121 comprising contributions from both maternal and fetal tissue. The maternal and mixed signals 120-121 from photodiodes 110-111 feed through a data acquisition unit 112 circuit that includes a trans-amplifier and an analog-to-digital (A/D) converter, which converts analog electrical signals from photodiodes 110-111 into a sequence of digital samples. These digital samples feed into processor 114, which performs a frequency-domain and/or time-domain filtering operation to remove maternal signal components from mixed signal 121 to produce a fetal signal (not illustrated), and then determines the fetal blood oxygenation level by performing a pulse-oximetry computation on the fetal signal. This process is described in more detail below.

During operation of the system illustrated in FIG. 1, LEDs 106 shine light through maternal tissue and onto fetus 104, which is typically located several centimeters below the skin. Arterial pulsations from the maternal and fetal heartbeats cause small changes in the tissue's light absorption, and is seen as slight changes in the diffuse reflectance when measured at the surface of maternal abdomen 102. By measuring this change in the diffused light signal, oximetry calculations are performed as described below.

As illustrated in FIG. 1, the photons seen at photodiode 111, which is further away from LEDs 106 than photodiode 110, contain both fetal and maternal signals. In contrast, the signals measured at smaller source-detector (SD) distances will be mostly maternal due to the formation of an optical shunt between the source and detector through the maternal tissue.

Figure 2:
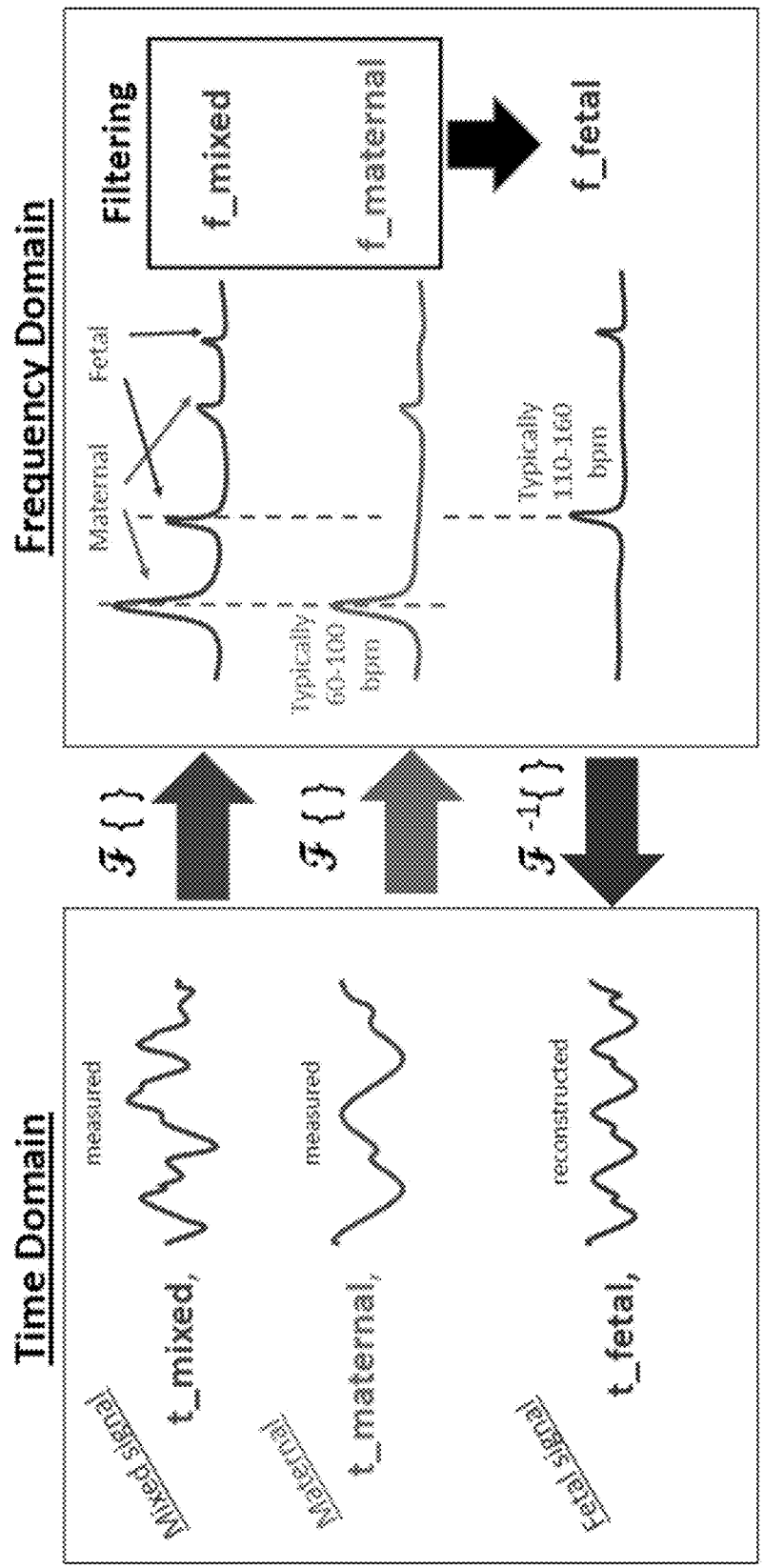
FIG. 2 illustrates how near and far detectors can be used to extract a fetal signal using frequency-domain filtering in accordance with the disclosed embodiments.

A number of techniques to extract the weak fetal signal from the mixed signal are currently under investigation. One approach is to use adaptive-filtering techniques, which are well-suited to noise-cancellation type problems. Another approach is through frequency-domain filtering. This is illustrated in FIG. 2, which presents a diagram showing how near-detectors and far-detectors can be used to extract the fetal signal by using frequency-domain filtering. Because the fetal heart rate (110-200 BPM) is typically faster than the maternal heart rate (60-100 BPM), each signal's primary and secondary harmonics can be seen as peaks in the power spectral density estimation. This makes it possible to remove the maternal contribution from the mixed signal.

The disclosed embodiments generally provide light-based techniques for measuring blood-oxygen saturation by performing calculations based on the Beer-Lambert Law (BLL), which describes light transmittance through a mixture of chromophores.

$$I = I_o * 10^{(-\Sigma \epsilon c L)} \quad (1)$$

In essence, equation (1) says that the incident light intensity $I_o$ decays ex-ponentially with respect to the concentration of chromophores in the medium c, their molar extinction coefficients E, and the path-length that a photon takes through the medium L.

Note that blood is one of the primary absorbers of light in human tissue. The main chromophores in red blood cells are a function of hemoglobin, namely oxyhemoglobin and deoxyhemoglobin ($HbO_2$ and $Hb$, respectively), which absorb light differently in the red and near-infrared region of light. Pulse oximetry utilizes arterial pulsations caused by the cardiac cycle to perform in vivo measurements of arterial oxygen saturation ($SaO_2$), which can be described by the following equation.

$$SaO_2 = \frac{[HbO_2]}{[HbO_2] + [Hb]} * 100\% \quad (2)$$

Note that each heartbeat causes a slight increase in the arterial blood volume, which results in a change to the tissue's light absorption. The change from pulsating tissues is referred to as the alternating-current (AC) signal, whereas the absorption from non-pulsating tissues is referred to as the direct-current (DC) signal. By defining a ratio R at two different wavelengths, as shown in Equation (3), a theoretical calculation of $SaO_2$ can be obtained. Note that the wavelengths chosen for calculating R should ideally lie on opposite sides of the isosbestic point of the absorption curve for $Hb$ and $HbO_2$ (e.g., 660 nm and 940 nm).

$$R = \frac{\log(I_{AC,\lambda_1}/I_{DC,\lambda_1})}{\log(I_{AC,\lambda_2}/I_{DC,\lambda_2})} \quad (3)$$

While useful as a theoretical explanation for pulse oximetry, this calculation assumes that only functional hemoglobin is in the blood and does not consider partial reflection at the skin surface and light scattering. Therefore, measurements from clinical-grade pulse oximeters ($SpO_2$) are empirically calibrated using in vivo measurement results from clinical studies to which the true arterial oxygen saturation ($SaO_2$) is calculated using a CO-oximeter or blood-gas analyzer.

Light Scattering Effects

Light scattering from particles is caused by gradients and discontinuities in the refractive index from the surrounding medium. When a photon scatters, its path-length increases, thereby increasing its likelihood of getting absorbed before being observed. The scattering coefficient, $\mu_s$ (units: $cm^{-1}$), is defined as the expected number of scattering events a photon goes through per unit path-length. Similarly, the absorption coefficient, $\mu_a$ (units: $cm^{-1}$), is the likelihood of photon absorption per unit path-length. Both are properties of the medium and are wavelength dependent. Note that the absorption coefficient, $\mu_a$ (units: $cm^{-1}$), is related to the molar extinction coefficient, $\epsilon$ (units: $cm^{-1}$/(moles per liter)), by the equation $\mu_a = \ln(10)*\epsilon*$(molar concentration). The anisotropy of scattering, g (units: a.u.), describes the expected angle at which photon scattering occurs. In highly scattering materials, photon propagation can be modeled as larger, more isotropic steps rather than small anisotropic steps. This larger step is described by the reduced scattering coefficient $\mu'_s$, defined as $\mu'_s = \mu_s(1-g)$.

In biological tissue, a photon will scatter many times before being absorbed or observed by a detector. In this case, the diffusion approximation of the Radiation Transport Equation (RTE) applies. While a rigorous explanation of the RTE is beyond the scope of this disclosure, an insight it gives is that the effective depth of penetration is approximately half the light source-detector (SD) distance for near-infrared light. However, the amount of light a detector sees decreases the further away it is from the source. Maximizing for both the depth-of-penetration and detected light objectives, as is the case for transabdominal fetal oximetry (TFO), creates an optimization problem, which calls for SD separation and wavelength to be tuned.

Problem Statement and Approach

In order to estimate fetal $SaO_2$ using TFO, an optical signal that contains a strong fetal component needs to be measured. Using diffusion theory, one concludes that increasing the SD distance improves signal sensitivity to the fetal layers, but degrades the strength of the fetal signal. Selecting an optimal wavelength that maximizes both parameters is challenging because of the scattering and the absorption coefficient's intimate dependence on wavelength for different layers of tissue.

The following discussion addresses this question. "In designing an optode for TFO, which wavelengths of light and SD distance should be used to optimally measure the fetal signal from a fetus located at depth x?" These determinations can be made by performing the following operations: (1) investigating the effect of wavelength and SD distance on fetal signal strength and signal sensitivity for various fetal depths using Monte Carlo simulations; (2) determining how to select an appropriate wavelength pair and SD distance to measure the fetal signal from a fetus at depth x using a low-cost photodetector and simulation results; and (3) validating the simulation results by developing an optical probe and data acquisition system and measuring values over two wavelengths using an optical phantom.

For clarity, the following terminology is used in the present disclosure. The term "mixed signal" refers to overall diffuse reflectance, and is made up of all photons that have traversed tissue and escaped at the surface of the maternal abdomen. The term "fetal signal" refers to the portion of the mixed signal that is attributed to photons that propagated to a fetal arterial layer. The term "signal sensitivity" refers to a ratio of photons attributed to the fetal signal with respect to the mixed signal. The term "fetal depth" refers to the combined thickness of maternal layers and amniotic fluid.

Monte Carlo Simulation

We use Monte Carlo simulation and convolution technique embodied in a simulator program written by Wang and Jacques, which simulates photon transport through a semi-infinite, multi-layered tissue. (See L. Wang et al., "Mcml—Monte Carlo modeling of light transport in multi-layered tissues," *Computer Methods and Programs in Biomedicine*, vol. 47, no. 2, pp. 131-146, 1995.) This program simulates the impulse response to a pencil-beam light source by injecting photons into the tissue and simulating the random scattering and absorption events that take place, until the photons escape the tissue or are absorbed. Physical quantities are then scored for post-simulation analysis. Due to the linear and translation-invariant properties of this system, the response can be convolved with another function to represent the response to a light source with a beam pattern of finite size. The experiments simulated a light source with a Gaussian beam pattern and looked at the diffuse reflectance ($W/cm^2$) and the proportion of photons that had probed the fetal arterial tissue.

Tissue Model

Figure 3A:
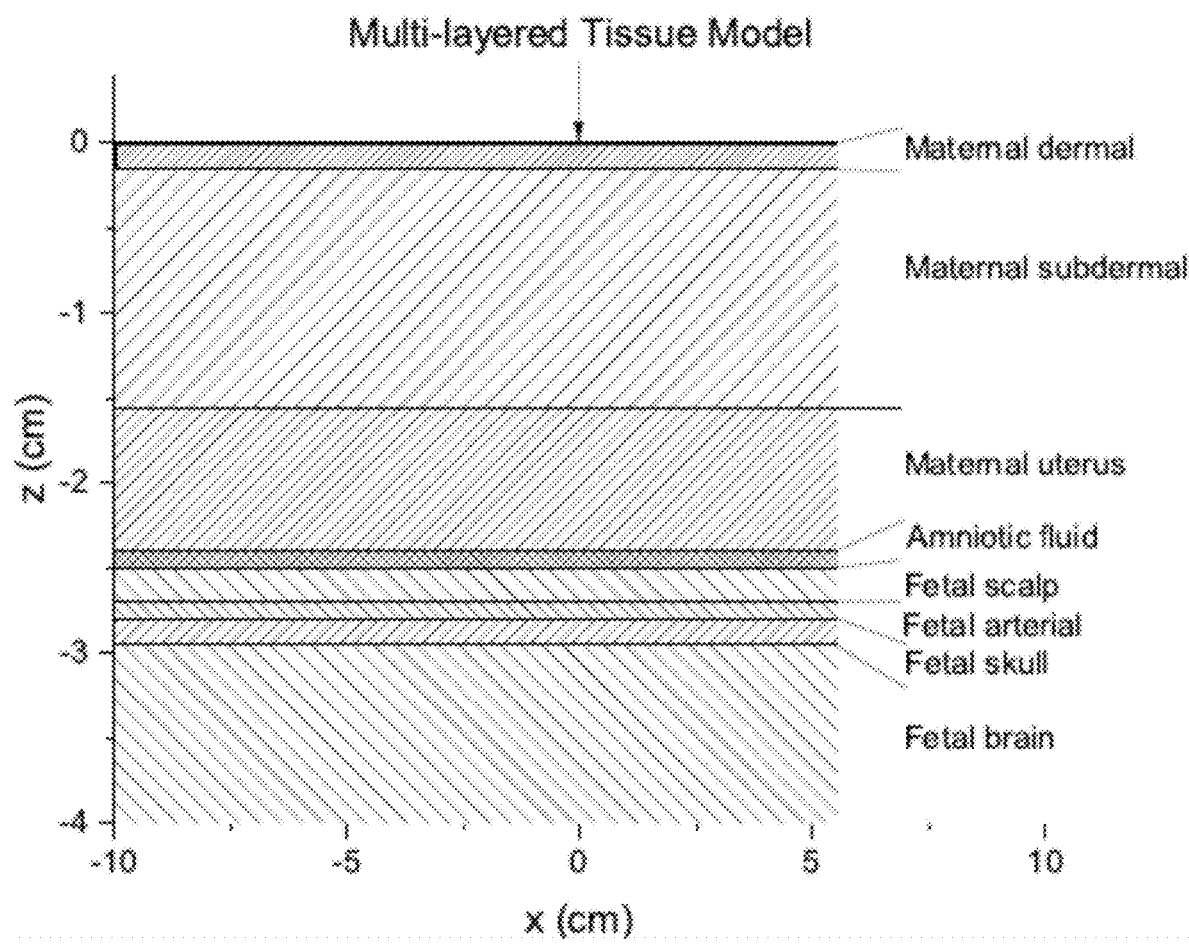
FIG. 3A illustrates a multi-layered tissue model in accordance with the disclosed embodiments.

To model light propagation in the intrapartum environment, a simplified tissue model was employed that includes three maternal layers (maternal dermal, subdermal, and uterine tissue), a layer for amniotic fluid, and four fetal layers (fetal scalp, fetal arterial, fetal skull, and fetal brain). Each layer is planar and semi-infinite and is illustrated in FIG. 3A. The physical and optical properties used for each layer and wavelength are taken from published works that investigated the properties using ex vivo and in vivo tissues. Each layer's absorption coefficient $\mu_a$ ($cm^{-1}$), reduced scattering coefficient $\mu'_s$ ($cm^{-1}$), and tissue thickness z (cm) can be seen in the table that appears in FIG. 3B. Note that the anisotropy of scattering g was assigned to 0.9 for all tissues, and the index of refraction (n) was 1.4 for maternal tissues, 1.334 for the amniotic fluid, and 1.3 for the fetal tissues. The fetal arterial layer was modeled after the superficial temporal artery during systolic events for an $SaO_2$ at 58% at a 10% blood-tissue volume, which are normal values for the fetus.

For each wavelength, the simulations investigated how fetal depth affects the strength of the fetal signal. This is useful for understanding inter-patient variability and feasibility of measuring a deeper fetal signal for an optode with a set SD distance. To evaluate device application during the active labor phase of delivery in which fetal head is very close to the mother's lower abdomen area, the simulations varied the thickness of the maternal subdermal layer to achieve fetal depths from 2 to 5 cm in 0.5 cm increments.

Wavelength Selection

To reduce the systemic error in oximetry measurements in low-oxygen environments (such as the uterus), Mannheimer suggested using wavelength pairs at 735 nm and 890 nm, whereas Zourabian, et al., suggested that wavelength pairs in the range of 670-700 nm and 850-900 nm are optimal. (See [Mannheimer1997] P. D. Mannheimer et al., "Wavelength selection for low-saturation pulse oximetry," IEEE Trans. on Biomedical Engineering, vol. 44, no. 3, March 1997, and see [Zourabian 2000] A. Zourabian, et al., "Trans-abdominal monitoring of fetal arterial blood oxygenation using pulse oximetry," JBO, vol. 5, no. 4, 2000.) As such, representative wavelengths were selected from these areas for analysis of their effect on the fetal signal strength and sensitivity. The wavelengths selected to model include 700, 735, 800, 850, and 900 nm due to their significance in optical oximetry devices and relative absorption in Hb and $HbO_2$.

Noise Limits of Electrical Components

Measurement of the fetal signal relies upon the careful selection of low-noise optical components and an understanding of their limitations. The situation in which the detector is unable to measure the fetal signal is a fundamental limit in tuning the optode's SD distance and wavelength. The minimum detectable power of a photodetector is defined by its responsivity R and noise-equivalent power (NEP). The responsivity R describes the amount of current generated by a photodetector when incident light hits it and has units of amps per watt. The NEP describes the minimum level of radiative power needed to be applied to the detector in order to obtain a signal-to-noise ratio (SNR) of one and has units of W/Hz. It accounts for the sources of noise specific to the detector (such as thermal and shot noise), and is normalized over the square root of the measurement bandwidth.

Recently, the production of large monolithic photodiodes has become cost-effective thanks to the economies of scale with the semiconductor manufacturing process. Large monolithic photodiodes with low-noise levels are attractive options for a low-cost TFO system. A typical NEP for such a photodiode is $1.2*10^{-14}$ W/Hz for wavelengths at 900 nm. The NEP at the other wavelengths can be found by linearly scaling the NEP at the reference wavelength with the desired wavelength using the following equation.

$$NEP(\lambda) = NEP_{ref} * \frac{R_{ref}}{R(\lambda)} \quad (4)$$

To determine the minimum detectable power, the NEP is multiplied by the square-root of the measurement bandwidth. See equation (5) below.

$$P_{min}(\lambda) = NEP(\lambda) * \sqrt{BW} \quad (5)$$

This means that for 900 nm light, the noise power is at $1.2*10^{-14}$ W at a 1 Hz measurement bandwidth (or $3.79*10^{-13}$ W at a 1 kHz measurement bandwidth). In other words, an optical signal of at least $1.2*10^{-14}$ W must be applied to the detector over 1 sec (or $3.79*10^{-13}$ W over 1 ms) in order to obtain a SNR greater than or equal to 1. The simulations used the minimum detectable power to describe the feasibility of measuring the fetal signal at various fetal depths.

Experimental Setup

Using the above-described tissue model, Monte Carlo simulations were run over the wavelengths of 700, 735, 800, 850, and 900 nm, for fetal depths between 2 to 5 cm in 0.5 cm increments. For each fetal depth and wavelength, a total of 25 million photons were simulated (5 million photons per run, 5 runs per wavelength). However, for the deeper fetal depths at 4.5 cm and 5.0 cm, respectively, a total of 75 million photons and 340 million photons were simulated to reach convergence. Each wavelength was represented as a high-power LED with a 1/e beam radius of 0.25 cm emitting 600 mW of radiative power. The light detector was presented as an FDS100 (Thorlabs, Inc.) photodiode with a measurement bandwidth of 1 kHz. The minimum detectable power at each wavelength was determined using equations (4) and (5). These were then normalized to the surface area of the detector for comparison with the fetal signal, which has units of W/cm². This helped the analysis by constraining the SD distance to ranges where it would be feasible to measure the fetal signal using the photodetector.

Results and Discussion

Figure 4B:
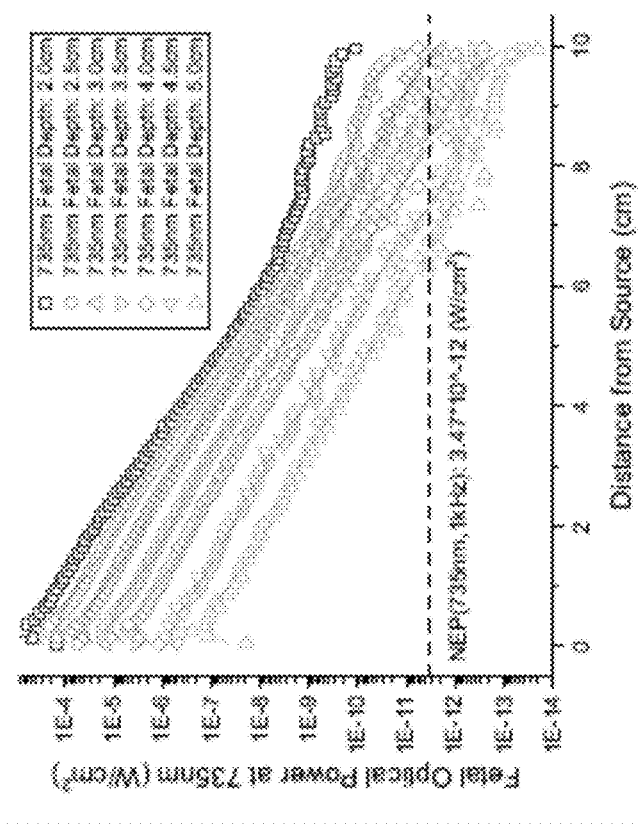
Figure 4A:
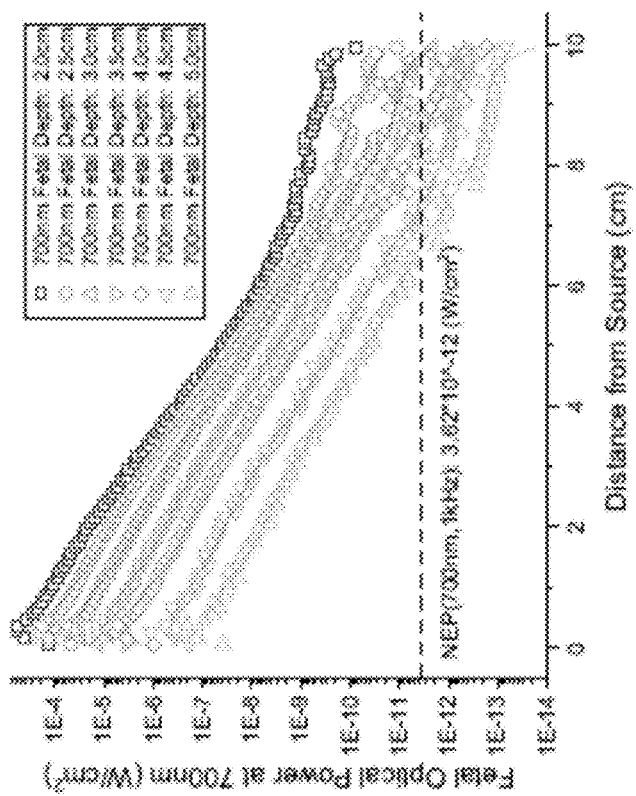
Figure 4D:
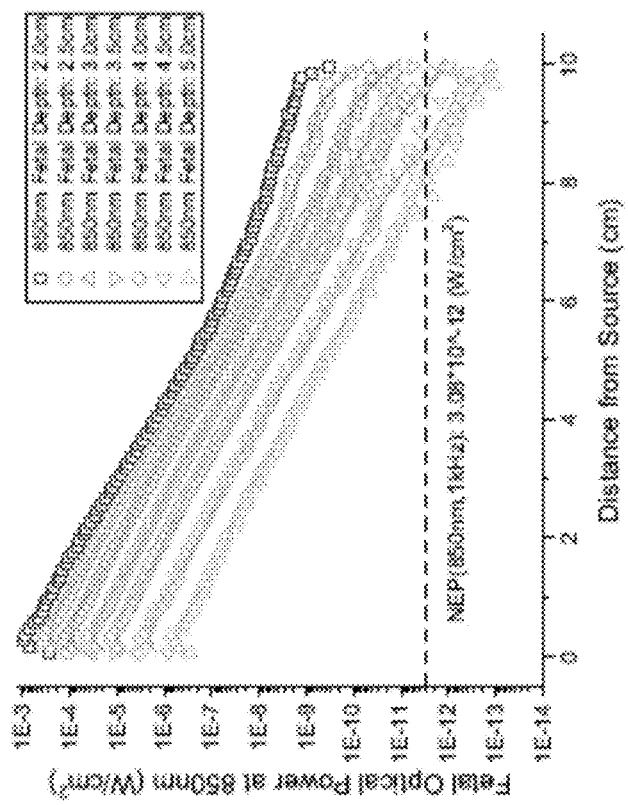
Figure 4C:
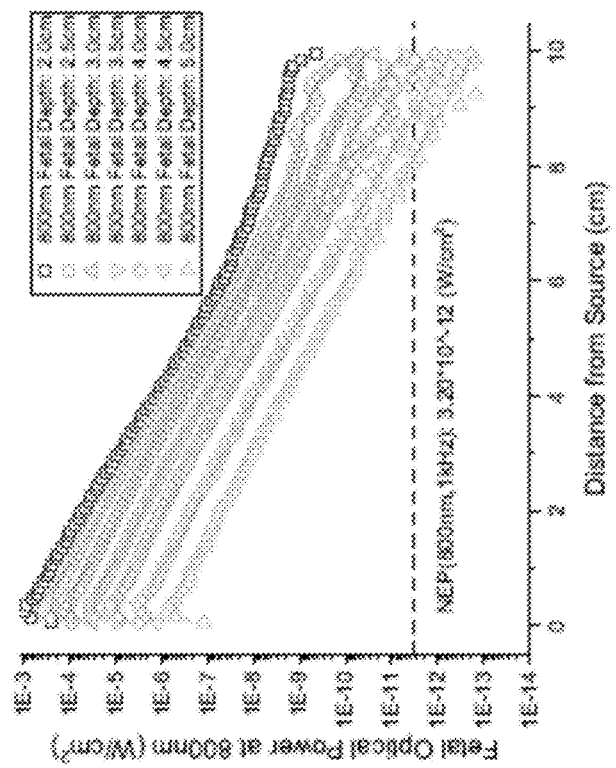

The relationship of the fetal signal with respect to the SD distance for various wavelengths and fetal depths can be seen in FIGS. 4A-4F. In each of FIGS. 4A-4F, the dashed line shows the minimum detectable power for an FDS100 (Thorlabs, Inc.) at that wavelength. This limits the distance the detector can be placed from the light source and still obtain a measurable optical signal that contains fetal information. More specifically, FIG. 4A shows the fetal optical signal for various fetal depths for a 700 nm wavelength of light, FIG. 4B for 735 nm, FIG. 4C for 800 nm, FIG. 4D for 850 nm, and FIG. 4E for 900 nm. FIG. 4F shows all five wavelengths of light when the fetal depth is 5.0 cm. As shown in FIGS. 4E-4F, when using 900 nm light, the largest SD distance that can be used while still being able to measure a fetal signal is 5.95 cm.

The fetal signal becomes weaker as the fetal depth increases at each wavelength of light. Interestingly, the strength of the 900 nm signal relative to other wavelengths changes with respect to fetal depth. For a fetal depth of 2.5 cm, the 900 nm signal ($1.336*10^{-9}$ W/cm²) is 1.710 times stronger than the 735 nm signal ($7.813*10^{-10}$ W/cm²). However, when the fetal depth increases to 5.0 cm, the 900 nm signal ($5.063*10^{-14}$ W/cm²) is much weaker than the 735 nm signal ($1.829*10^{-12}$), namely 3.612 times weaker, and limits the farthest the detector can be placed from the source, i.e., 5.95 cm. For the purposes of oximetry, the 900 nm light source could instead be swapped for an 850 nm light source, because they both are on the right-hand side of the isosbestic point, and 850 nm has a much stronger fetal signal. The SD distance is then limited by the 700/735 nm wavelengths, which allows the detector to be placed a maximum of 6.61 cm away from the light source while still being able to measure the fetal signal. If one selects the wavelengths 700 and 850 nm, the systemic error can also be minimized in oxygen calculations. (See [Zourabian 2000].) Note that the LEDs must be placed in close proximity to each other to keep the photon path-lengths of each wavelength relatively the same (and thus investigate the same tissue) to calculate the fetal $SaO_2$.

Figure 5D:
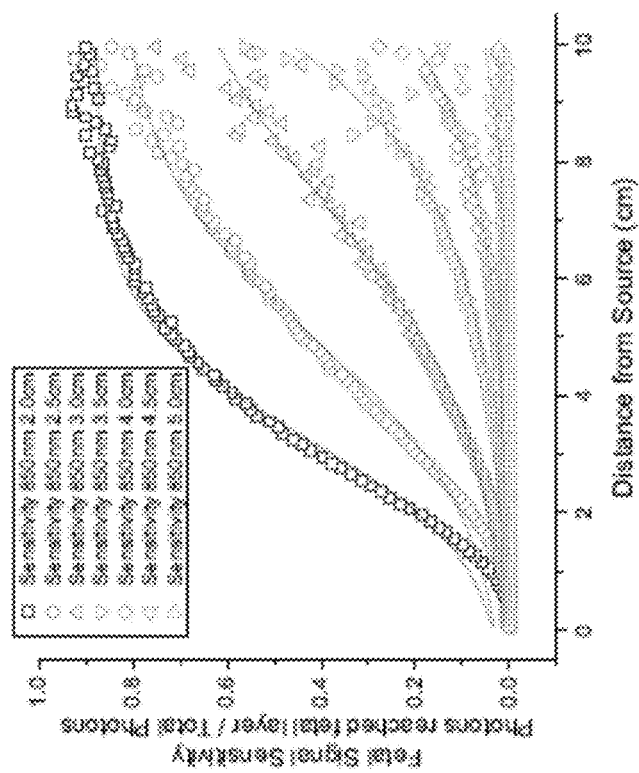
Figure 5C:
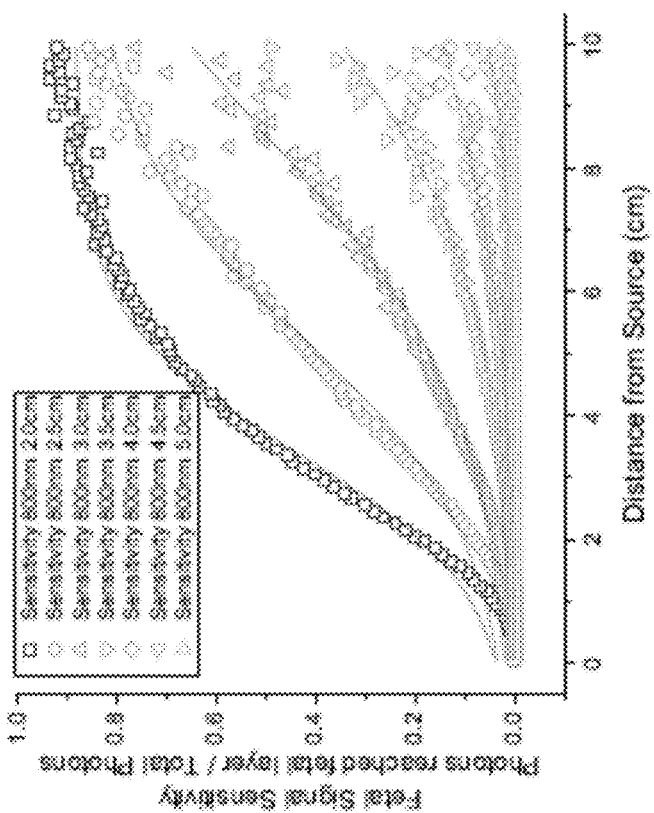
Figures 5E, 5F:
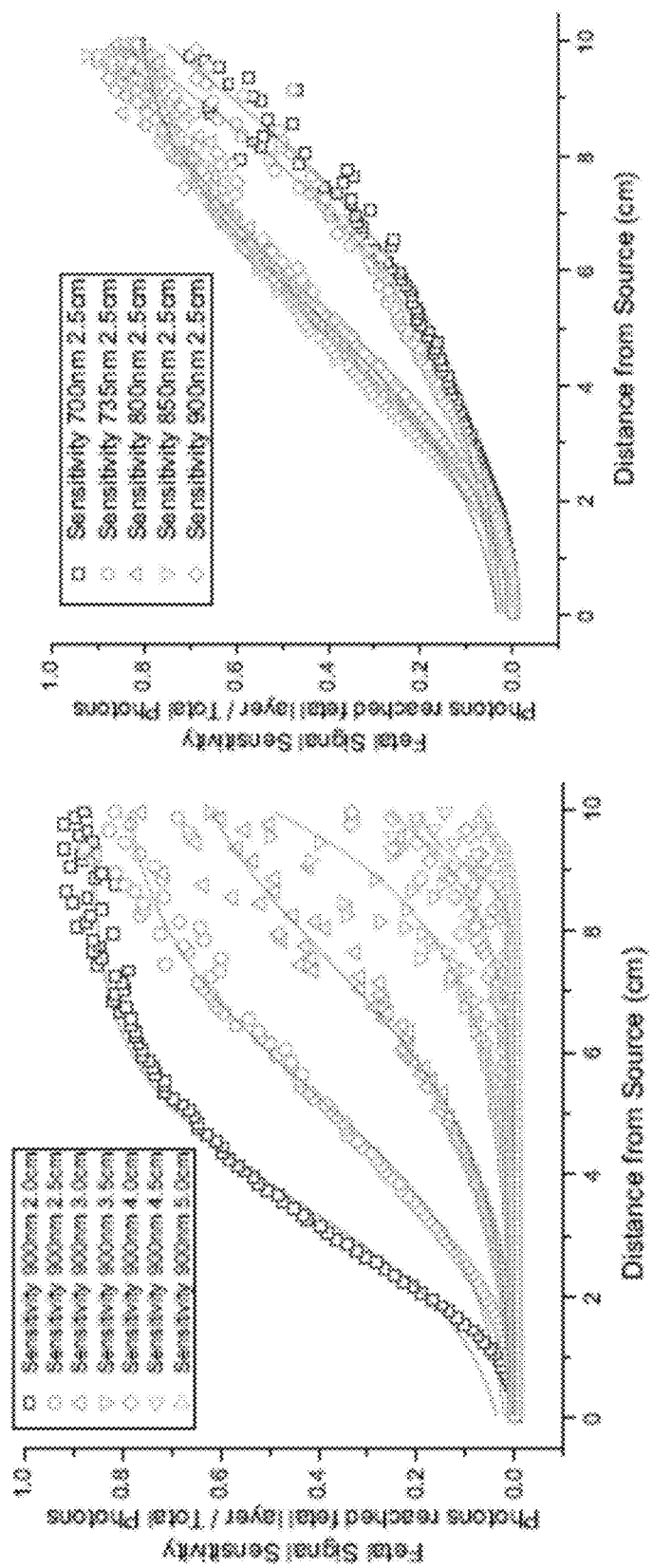

As illustrated in FIGS. 4A-4F, an intuitive approach towards increasing signal strength is to simply move the detector closer to the source. Unfortunately, the effect of signal sensitivity limits the usefulness of this approach. The signal sensitivity with respect to SD distance for various wavelengths and fetal depths can be seen in FIGS. 5A-5F. Signal sensitivity to the fetal layer is defined as the proportion of photons that have traversed the fetal arterial layer to the total number of photons seen. FIG. 5A shows the signal sensitivity for different fetal depths for 700 nm light, FIG. 5B for 735 nm, FIG. 5C for 800 nm, FIG. 5D for 850 nm, and FIG. 5E for 900 nm. FIG. 5F shows the signal sensitivity when the fetal depth is at 2.5 cm. As illustrated, the longer wavelengths of light (800 nm, 850 nm, and 900 nm) are more sensitive to the deeper fetal layer.

Figure 6:
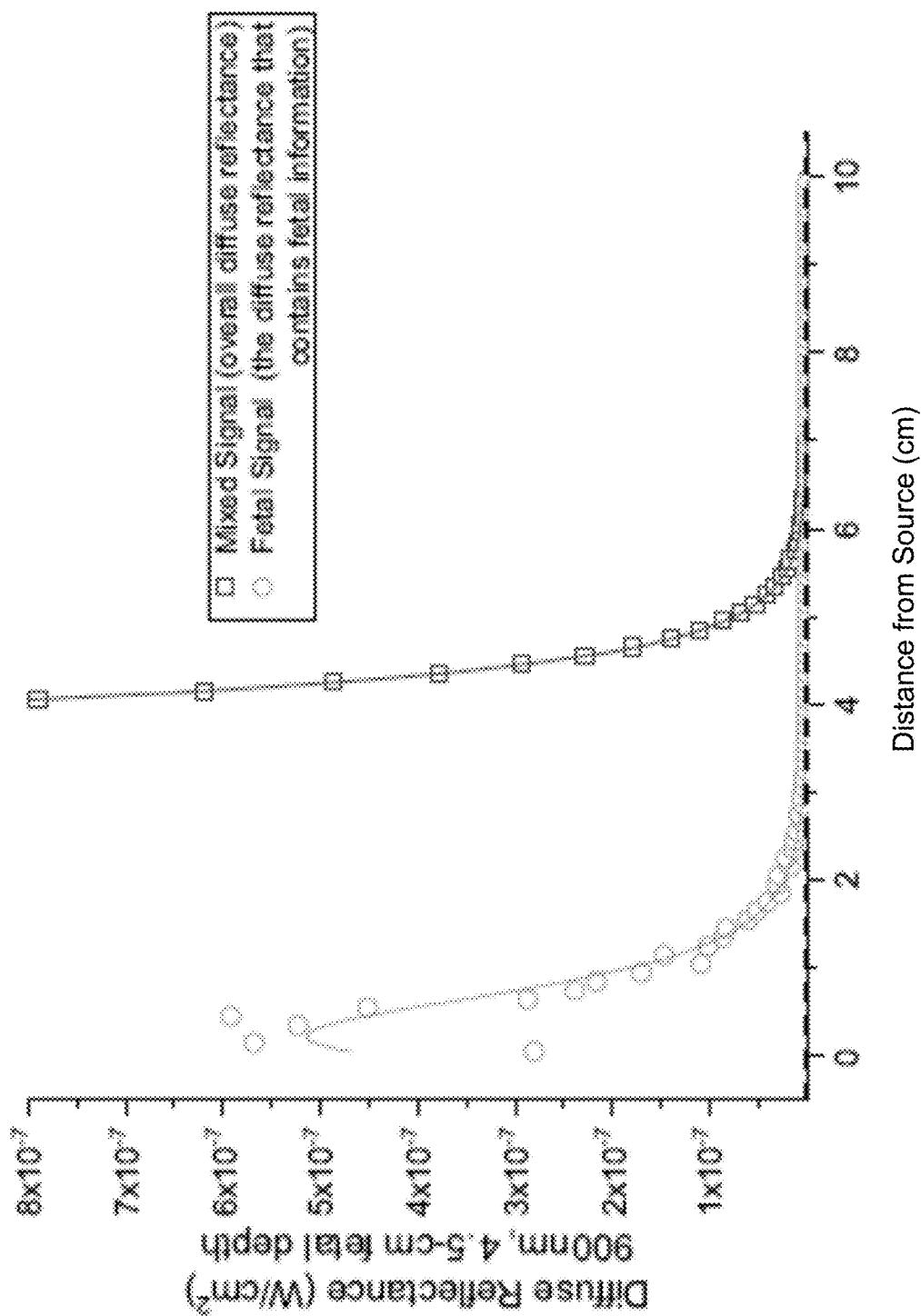
FIG. 6 presents a graph comparing a fetal signal with a mixed signal in accordance with the disclosed embodiments.

The mixed signal contains two types of photons: ones that traversed maternal tissues only, called Type 1, and those that traversed both fetal and maternal tissues, called Type 2. At shorter SD distances, an optical shunt is formed where Type 1 photons overwhelm the number of Type 2 photons, which contain the fetal information. Therefore, to minimize this effect the SD distance must be maximized, while still being able to detect enough Type 2 photons to stay above the minimum detectable power. Viewing the mixed signal in relation to the fetal signal on the linear graph shown in FIG. 6 helps to illustrate this point. More specifically, FIG. 6 illustrates the fetal signal versus the mixed signal for 900 nm light when the fetal depth is 4.5 cm. Note that a majority of photons detected at short SD distances do not traverse the fetal tissue.

Our results show that the optimal wavelength pairs to select for maximizing the strength of the fetal signal are 735 nm and 850 nm for the fetal depths described here. Moreover, the SD distance should then be increased to operate near the minimum detectable power to increase the signal sensitivity to the deeper tissue layers that contain fetal information.

Preliminary Results with Optical Phantom

To validate our simulation results, an optode was developed using high-power LEDs with peak wavelengths at 890 nm and 735 nm and a monolithic low-noise photodiode, whose minimum detectable power at those wavelengths is $5.573*10^{-13}$ W and $7.148*10^{-13}$ W, respectively. The approach was to measure the difference in strength of the fetal signal at the two wavelengths and then compare with the simulation results.

To interact with the optode, a data acquisition board was created and software was developed for data capture, analysis, and real-time visualization of the photodetector measurements. The LEDs were time-multiplexed to allow the real-time collection of both signals for comparison, where the SD distance was set at 7 cm. Light attenuation from the maternal layers involved using a 2.7 cm thick optical phantom made of bovine tissue. To evaluate the fetal signal strength, the diffuse reflected light was measured through the phantom placed upon a volunteer, which emulated the pulsating fetal tissue. After a one-minute sampling session, the strength of the fetal signal at the different wavelengths was measured. The fetal signal was identified in the frequency domain via the HR of the volunteer, validated using a clinical-grade pulse oximeter (Radical-7, Masimo). These simulation results highlight the fact that using 890 nm light should increase the fetal signal by 1.710 times over the fetal signal at 735 nm at a 2.5 cm fetal depth. Note that the fetal pulse at 890 nm was 1.543 times stronger than the 735 nm signal, indicating that the experimental results correlate well with the simulation.

Conclusion

The above-presented results show that selecting an appropriate wavelength and SD distance is fundamental to the development of a TFO system to optimally measure the fetal signal at varying fetal depths. A strong fetal signal can be measured using 735 nm and 850 nm wavelengths of light, and signal sensitivity can be improved by increasing the SD distance while staying above the minimum detectable power of the detector. Given the dynamic nature of fetus position in the uterus, it is imperative for the system to dynamically adjust its operation to be able to robustly extract fetal signal.

Process of Determining a Fetal Blood Oxygenation Level

Figure 7:
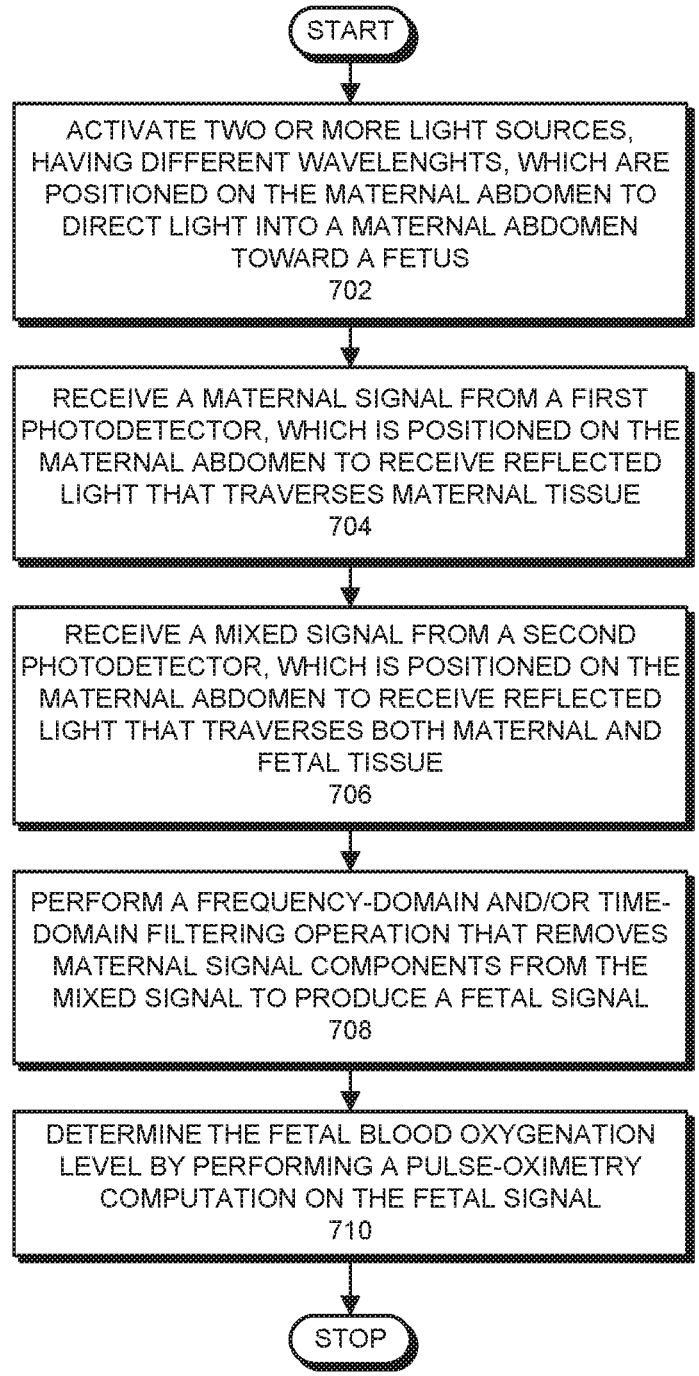
FIG. 7 presents a high-level flow chart illustrating operations the system performs while determining a fetal blood oxygenation level in accordance with the disclosed embodiments.

FIG. 7 presents a high-level flow chart illustrating operations the system performs while determining a fetal blood oxygenation level in accordance with the disclosed embodiments. First, the system activates two or more light sources, having different wavelengths, which are positioned on the maternal abdomen to direct light into the maternal abdomen toward a fetus (step 702). Next, the system receives a maternal signal from a first photodetector, which is positioned on the maternal abdomen to receive reflected light that traverses maternal tissue (step 704). The system also receives a mixed signal from a second photodetector, which is positioned on the maternal abdomen to receive reflected light that traverses both maternal and fetal tissue (step 706). The system then performs a frequency-domain and/or time-domain filtering operation that removes maternal signal components from the mixed signal to produce a fetal signal (step 708). Finally, the system determines the fetal blood oxygenation level by performing a pulse-oximetry computation on the fetal signal (step 710).

Figure 8A:
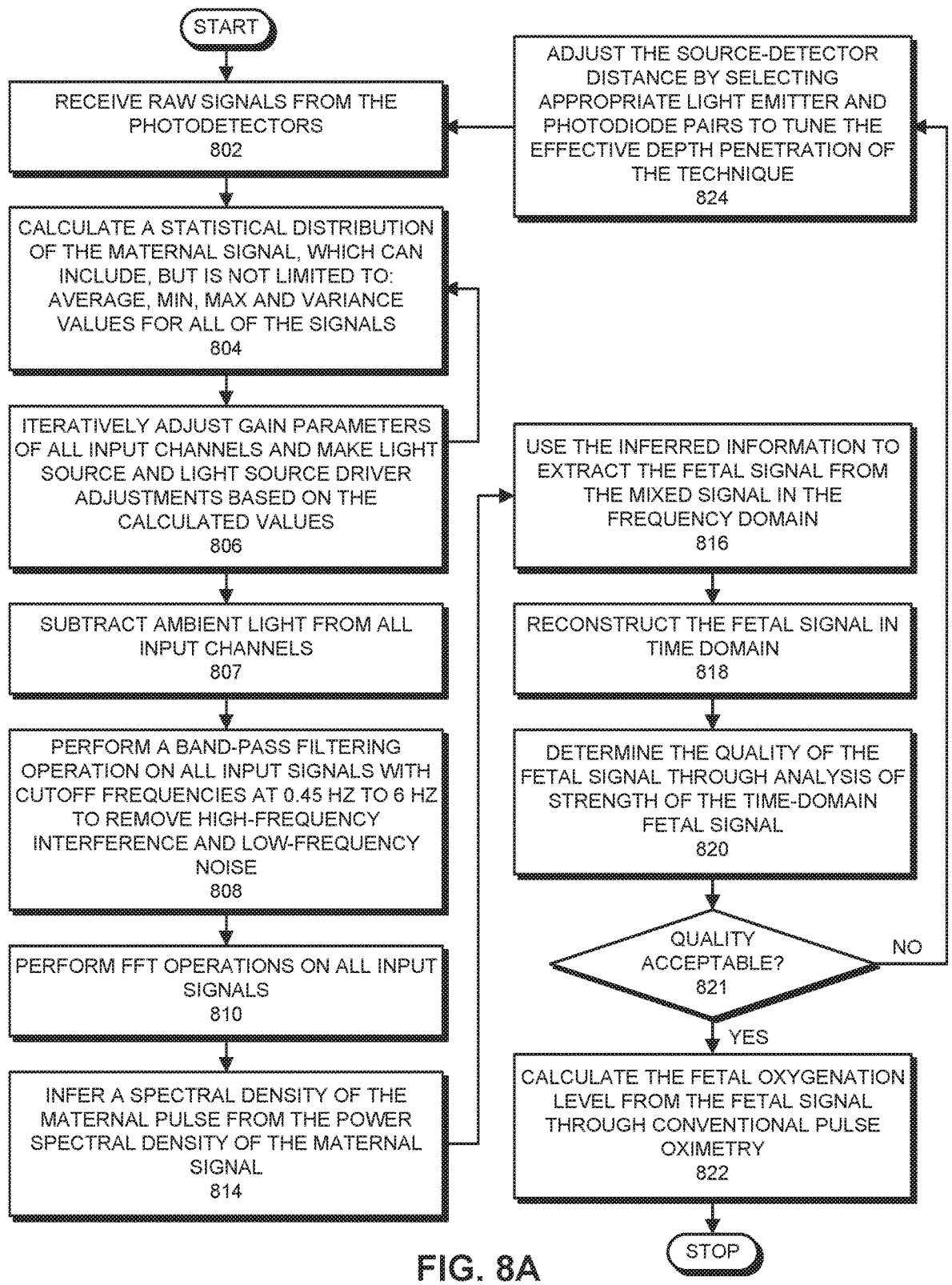
FIG. 8A presents a more-detailed flow chart illustrating operations the system performs while determining a fetal blood oxygenation level with frequency-domain filtering in accordance with the disclosed embodiments.

FIG. 8A presents a more-detailed flow chart illustrating operations the system performs while determining a fetal blood oxygenation level with frequency-domain filtering in accordance with the disclosed embodiments. First, the system receives raw signals from the photodetectors (step 802). Next, the system calculates a statistical distribution of the maternal signal, which can include, but is not limited to: average, minimum, maximum and variance values for all of the signals (step 804). The system then iteratively adjusts gain parameters of all input channels and make light source and light source driver adjustments based on the calculated statistical distribution of the maternal signal to utilize the full dynamic range of the data acquisition electronics (step 806). (Note that this iterative process may involve returning to step 804 if necessary.) The gain parameters can include component values of a transimpedance amplifier, a DC-level voltage bias, and a light emitter strength.

Next, the system subtracts ambient light from all of the input signals (step 807). Note that the ambient light can be subtracted so that the resulting signals only account for light received for the emitters at the appropriate wavelengths of light associated with the emitters. The system then performs a band-pass filtering operation on all input signals with cutoff frequencies at 0.45 Hz to 6 Hz to remove high-frequency interference and low-frequency noise (step 808). Note that such noise can be generated by power lines and low-frequency biosignals, such as signals associated with respiration and Mayer waves. Next, the system performs FFT operations on all of the input signals to convert the input signals into corresponding frequency-domain representations (step 810). The system then infers a spectral density of the maternal pulse from the power spectral density of the maternal signal (step 814).

Next, the system uses the inferred information to extract the fetal signal from the mixed signal (step 816). This can be done in a number of ways. (1) The system can use the inferred information to dynamically create and apply a notch filter having a notch frequency at the maternal heart rate, wherein the fetal signal is extracted by analyzing the power spectral density of the filtered signal. (2) The system can use the inferred information to analyze the mixed signal to infer the fetal heart rate by comparing the differences in the normalized power spectral density between the maternal signal and the mixed signal. The system can then apply a high-pass filter with a cutoff frequency between the maternal heart rate and fetal heart rate. (3) The system can use the inferred information to examine higher frequencies for the fetal heart rate, which should lie between the first and second harmonics of the power spectral density of the maternal heart rate. The system can then extract the fetal signal by applying a band-pass filter with cutoff frequencies between the first and the second harmonics of the maternal heart rate, and the fetal heart rate.

The system then reconstructs the fetal signal in the time domain (step 818). After the fetal signal is reconstructed, the system can determine the quality of the fetal signal through analysis of the strength of the time-domain fetal signal (step 820). The system then determines whether the quality is acceptable (step 821). If the quality is acceptable (YES at step 821), the system calculates the fetal oxygenation level from the fetal signal through conventional pulse oximetry (step 822), and the process is complete. Otherwise (NO at step 821), the system can adjust the source-detector distance by selecting appropriate light emitter and photodiode pairs to tune the effective depth penetration of the technique (step 824). Note that the system can generally include multiple light emitters and multiple photodiodes placed at various sites on the maternal abdomen. This enables the system to extract and analyze multiple fetal signals from different source-detector pairs, and to select appropriate pairs to tune the effective depth of penetration of the technique. The system then returns to step 802 to repeat the process.

Figure 8B:
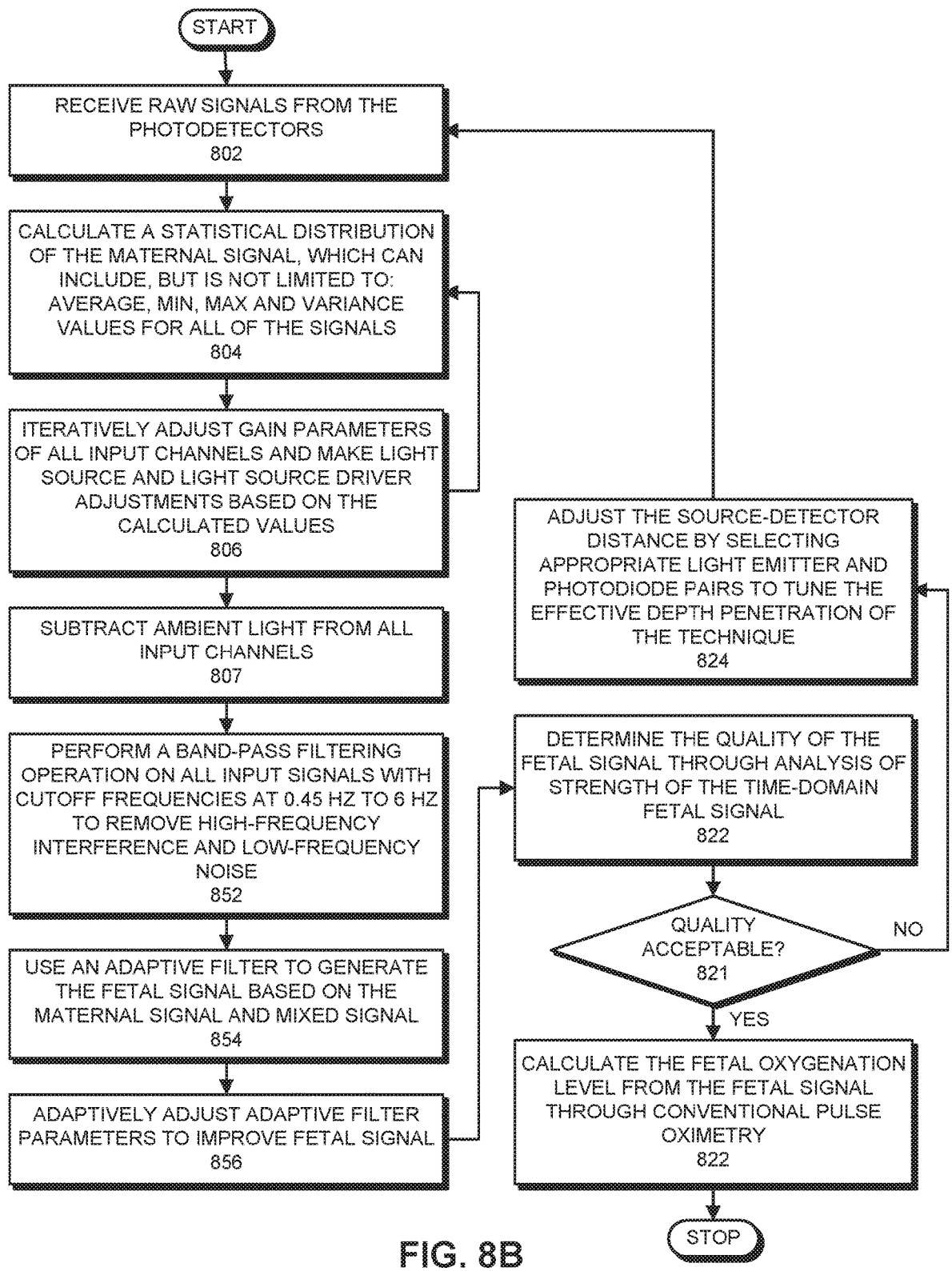
FIG. 8B presents a more-detailed flow chart illustrating operations the system performs while determining a fetal blood oxygenation level with time-domain filtering in accordance with the disclosed embodiments.

FIG. 8B presents a more-detailed flow chart illustrating operations the system performs while determining a fetal blood oxygenation level with time-domain filtering in accordance with the disclosed embodiments. This flow chart is the same as the flow chart in FIG. 8A except that steps 808-818 have been replaced with steps 852-856. In step 850, the system subtracts ambient light from all of the input signals. Next, the system performs a band-pass filtering operation on all input signals with cutoff frequencies at 0.45 Hz to 6 Hz to remove high-frequency interference and low-frequency noise (step 852). Then, the system uses an adaptive filter to generate the fetal signal based on the mixed signal and the maternal signal (step 854). Next, the system adaptively adjusts the adaptive filter to improve the fetal signal (step 856). This involves dynamically adjusting adaptive filter parameters to respond to the dynamic nature of variations in the input signals. During this process, the system scales the parameters of the maternal signal so that it best matches its replica in the mixed signal, and then subtracts the scaled and filtered version from the mixed signal, which yields the fetal signal. The system then proceeds to step 820 where it determines the quality of the fetal signal.

Various modifications to the disclosed embodiments will be readily apparent to those skilled in the art, and the general principles defined herein may be applied to other embodiments and applications without departing from the spirit and scope of the present invention. Thus, the present invention is not limited to the embodiments shown, but is to be accorded the widest scope consistent with the principles and features disclosed herein.

The foregoing descriptions of embodiments have been presented for purposes of illustration and description only. They are not intended to be exhaustive or to limit the present description to the forms disclosed. Accordingly, many modifications and variations will be apparent to practitioners skilled in the art. Additionally, the above disclosure is not intended to limit the present description. The scope of the present description is defined by the appended claims.

What is claimed is:

1. A method for determining a fetal blood oxygenation level, comprising:
activating two or more light sources, having different wavelengths, which are positioned on the maternal abdomen of a pregnant mammal to direct light into a maternal abdomen toward a fetus;
receiving a maternal signal from a first photodetector, which is positioned on the maternal abdomen to receive reflected light that traverses maternal tissue;
receiving a mixed signal from a second photodetector, which is positioned on the maternal abdomen to receive reflected light that traverses both maternal and fetal tissue;
dynamically adjusting one or more of the maternal signal and the mixed signal by:
calculating a statistical distribution, which can include, but is not limited to: average, minimum, maximum and variance values for the one or more of the maternal signal and the mixed signal; and
adjusting a gain of an amplifier for the one or more of the maternal signal and the mixed signal based on the calculated statistical distribution;
performing a filtering operation that removes maternal signal components from the mixed signal to produce a fetal signal; and
determining the fetal blood oxygenation level by performing a pulse-oximetry computation on the fetal signal.

2. The method of claim 1, wherein the filtering operation discriminates between the maternal and fetal signals based on periodic variations in the maternal and fetal signals caused by arterial pulsations that are correlated with maternal and fetal heartbeats.

3. The method of claim 2, wherein performing the filtering operation comprises:
performing fast-Fourier transform (FFT) operations on the mixed and maternal signals to compute corresponding frequency-domain representations of the mixed and maternal signals;
inferring a maternal spectral density and heart rate from the frequency-domain representation of the maternal signal; and
using the inferred maternal spectral density and heart rate to filter out the maternal signal from the mixed signal to produce the fetal signal.

4. The method of claim 3, wherein the method further comprises improving the fetal signal by adaptively adjusting filter parameters used to filter out the maternal signal.

5. The method of claim 1, wherein:
the two or more light sources emit light at two or more different wavelengths, including wavelengths $\lambda_1$ and $\lambda_2$, which lie on opposite sides of an isosbestic point of an absorption curve for Hb and $HbO^2$; and
the pulse oximetry computation is performed on an AC component of the fetal signal associated with pulsating fetal tissue, which includes blood, for each of the wavelengths $\lambda_1$ and $\lambda_2$, and a DC component of the fetal signal associated with non-pulsating fetal tissue for each of the wavelengths $\lambda_1$ and $\lambda_2$.

6. The method of claim 5, wherein:
the wavelength $\lambda_1$ substantially equals 735 nm; and
the wavelength $\lambda_2$ substantially equals 850 nm.

7. The method of claim 1, wherein after the fetal signal is produced, the method further comprises adjusting a source-detector distance by:
determining a quality of the fetal signal through analysis of the strength of the fetal signal compared to noise in the time-domain; and
tuning an effective depth of penetration for the method by selecting a light-source-and-photodetector pair from a plurality of light sources and plurality of photodetectors located at different sites on the maternal abdomen, wherein the selection is based on the determined qualities of fetal signals associated with different light-source-and-photodetector pairs.

8. The method of claim 1, wherein after the fetal signal is produced, the method further comprises adjusting a source-detector distance by:
determining a quality of the fetal signal through analysis of the strength of the fetal signal compared to noise in the frequency-domain; and
tuning an effective depth of penetration for the method by selecting a light-source-and-photodetector pair from a plurality of light sources and plurality of photodetectors located at different sites on the maternal abdomen, wherein the selection is based on the determined qualities of fetal signals associated with different light-source-and-photodetector pairs.

9. The method of claim 1, wherein the method further comprises:
measuring one or more of, a fetal heart rate, a maternal heart rate, and a maternal blood oxygenation level using one or more other measurement devices; and using one or more of the measured fetal heart rate, the measured maternal heart rate and/or the measured maternal blood oxygenation level while determining the fetal blood oxygenation level.

10. The method of claim 1, wherein the two or more light sources include two or more near-infrared light-emitting diodes (LEDs) that emit light at two or more wavelengths.

11. The method of claim 1, wherein the first and second photodetectors comprise silicon photodiodes.

12. The method of claim 1, wherein the fetal blood oxygenation level is equivalent to the fetal hemoglobin oxygen saturation level.

13. A system that determines a fetal blood oxygenation level, comprising:
two or more light sources, having different wavelengths, to be positioned on a maternal abdomen of a pregnant mammal to direct light into a maternal abdomen toward a fetus;
a controller to selectively activate the two or more light sources;
a first photodetector to be positioned on the maternal abdomen to receive reflected light that traverses maternal tissue to produce a maternal signal;
a second photodetector to be positioned on the maternal abdomen to receive reflected light that traverses both maternal and fetal tissue to produce a mixed signal; and
a processing mechanism that:
receives the maternal signal and the mixed signal,
dynamically adjusts one or more of the maternal signal and the mixed signal by:
calculating a statistical distribution, which can include, but is not limited to: average, minimum, maximum and variance values for the one or more of the maternal signal and the mixed signal, and
adjusting a gain of an amplifier for the one or more of the maternal signal and the mixed signal based on the calculated statistical distribution,
performs a filtering operation to remove maternal signal components from the mixed signal to produce a fetal signal, and
determines the fetal blood oxygenation level by performing a pulse-oximetry computation on the fetal signal.

14. The system of claim 13, wherein the filtering operation discriminates between the maternal and fetal signals based on periodic variations in the maternal and fetal signals caused by arterial pulsations that are correlated with maternal and fetal heartbeats.

15. The system of claim 14, wherein while performing the filtering operation, the processing mechanism:
performs fast-Fourier transform (FFT) operations on the mixed and maternal signals to compute corresponding frequency-domain representations of the mixed and maternal signals;
infers a maternal spectral density and heart rate from the frequency-domain representation of the maternal signal; and
uses the inferred maternal spectral density and heart rate to filter out the maternal signal from the mixed signal to produce the fetal signal.

16. The system of claim 15, wherein the processing mechanism is configured to improve the fetal signal by adaptively adjusting filter parameters used to filter out the maternal signal.

17. The system of claim 13, wherein:
the two or more light sources emit light at two or more different wavelengths, including wavelengths $\lambda_1$ and $\lambda_2$, which lie on opposite sides of an isosbestic point of an absorption curve for Hb and $HbO^2$; and
the processing mechanism is configured to perform the pulse oximetry computation on an AC component of the fetal signal associated with pulsating fetal tissue, which includes blood, for each of the wavelengths $\lambda_1$ and $\lambda_2$, and a DC component of the fetal signal associated with non-pulsating fetal tissue for each of the wavelengths $\lambda_1$ and $\lambda_2$.

18. The system of claim 17, wherein:
the wavelength $\lambda_1$ substantially equals 735 nm; and
the wavelength $\lambda_2$ substantially equals 850 nm.

19. The system of claim 13, wherein after the fetal signal is produced, the processor adjusts a source-detector distance by:
determining a quality of the fetal signal through analysis of the strength of the fetal signal compared to noise in the time-domain; and
tuning an effective depth of penetration for the system by selecting a light-source-and-photodetector pair from a plurality of light sources and plurality of photodetectors located at different sites on the maternal abdomen, wherein the selection is based on the determined qualities of fetal signals associated with different light-source-and-photodetector pairs.

20. The system of claim 13, wherein after the fetal signal is produced, the processor adjusts a source-detector distance by:
determining a quality of the fetal signal through analysis of the strength of the fetal signal compared to noise in the frequency-domain; and
tuning an effective depth of penetration for the system by selecting a light-source-and-photodetector pair from a plurality of light sources and plurality of photodetectors located at different sites on the maternal abdomen, wherein the selection is based on the determined qualities of fetal signals associated with different light-source-and-photodetector pairs.

21. The system of claim 13, wherein:
the system additionally comprises one or more other measurement devices, which are configured to measure one or more of, a fetal heart rate, a maternal heart rate, and a maternal blood oxygenation level; and
the processing mechanism is configured to use one or more of the measured fetal heart rate, the measured maternal heart rate and/or the measured maternal blood oxygenation level while determining the fetal blood oxygenation level.

22. The system of claim 13, wherein the two or more light sources include two or more near-infrared light-emitting diodes (LEDs) that emit light at two or more wavelengths.

23. The system of claim 13, wherein the first and second photodetectors comprise silicon photodiodes.

24. The system of claim 13, wherein the fetal blood oxygenation level is equivalent to the fetal hemoglobin oxygen saturation level.

25. A non-transitory, computer-readable storage medium storing instructions that when executed by a computer cause the computer to perform a method for determining a fetal blood oxygenation level, the instructions comprising:
instructions for activating two or more light sources, which are positioned on the maternal abdomen of a pregnant mammal to direct light into a maternal abdomen toward a fetus;

instructions for receiving a maternal signal generated by a first photodetector, which is positioned on the maternal abdomen to receive reflected light that traverses maternal tissue;

instructions for receiving a mixed signal generated by a second photodetector, which is positioned on the maternal abdomen to receive reflected light that traverses both maternal and fetal tissue;

instructions for dynamically adjusting one or more of the maternal signal and the mixed signal by:

calculating a statistical distribution, which can include, but is not limited to: average, minimum, maximum and variance values for the one or more of the maternal signal and the mixed signal; and adjusting a gain of an amplifier for the one or more of the maternal signal and the mixed signal based on the calculated statistical distribution;

instructions for performing a filtering operation that removes maternal signal components from the mixed signal to produce a fetal signal; and instructions for determining the fetal blood oxygenation level by performing a pulse-oximetry computation on the fetal signal.

26. The non-transitory, computer-readable storage medium of claim 25, wherein the fetal blood oxygenation level is equivalent to the fetal hemoglobin oxygen saturation level.

27. A method for determining a fetal blood oxygenation level, comprising:

activating multiple light sources placed at various sites on a maternal abdomen of a pregnant mammal, wherein the multiple light sources are positioned to direct light into the maternal abdomen toward a fetus;

receiving signals from multiple photodetectors placed at various sites on the maternal abdomen, wherein:

one or more maternal signals are received from one or more photodetectors in the multiple photodetectors, which are positioned on the maternal abdomen to receive reflected light that traverses maternal tissue, and one or more mixed signals are received from one or more photodetector in the multiple photodetectors, which are positioned on the maternal abdomen to receive reflected light that traverses both maternal and fetal tissue;

performing a filtering operation that removes maternal signal components from the mixed signals to produce corresponding fetal signals;

analyzing multiple fetal signals received from different light-source- photodetector pairs;

selecting one or more light-source-photodetector pairs based on the analysis to tune an effective depth of penetration of the method; and determining the fetal blood oxygenation level by performing a pulse-oximetry computation on fetal signals received from the selected light-source-photodetector pairs.

28. The method of claim 27, wherein the fetal blood oxygenation level is equivalent to the fetal hemoglobin oxygen saturation level.

29. The method of claim 27, wherein the filtering operation discriminates between the one or more maternal signals and the fetal signals based on periodic variations in the maternal and fetal signals caused by arterial pulsations that are correlated with maternal and fetal heartbeats.

30. The method of claim 27, wherein the filtering operation comprises:

performing fast-Fourier transform (FFT) operations on the one or more mixed signals and the one or more maternal signals to compute corresponding frequency-domain representations of the mixed and maternal signals;

inferring a maternal spectral density and heart rate from the frequency- domain representation of the maternal signals; and using the inferred maternal spectral density and heart rate to filter out the one or more maternal signals from the one or more mixed signals to produce the fetal signals.

31. The method of claim 30, further comprising improving the fetal signals by adaptively adjusting filter parameters used to filter out the one or more maternal signals.

32. The method of claim 27, wherein:

the multiple light sources emit light at two or more different wavelengths, including wavelengths $\lambda_1$ and $\lambda_2$, which lie on opposite sides of an isosbestic point of an absorption curve for Hb and $HbO^2$; and the pulse oximetry computation is performed on an AC component of the fetal signals associated with pulsating fetal tissue, which includes blood, for each of the wavelengths $\lambda_1$ and $\lambda_2$, and a DC component of the fetal signals associated with non-pulsating fetal tissue for each of the wavelengths $\lambda_1$ and $\lambda_2$.

* * * * *